United States Patent
Boppart et al.

(10) Patent No.: US 9,867,528 B1
(45) Date of Patent: Jan. 16, 2018

(54) QUANTITATIVE PNEUMATIC OTOSCOPY USING COHERENT LIGHT RANGING TECHNIQUES

(71) Applicant: Board of Trustees of the University of Illinois, Urbana, IL (US)

(72) Inventors: Stephen A. Boppart, Champaign, IL (US); Ryan Shelton, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 813 days.

(21) Appl. No.: 14/303,134

(22) Filed: Jun. 12, 2014

Related U.S. Application Data

(60) Provisional application No. 61/869,805, filed on Aug. 26, 2013.

(51) Int. Cl.
*A61B 6/00* (2006.01)
*A61B 1/227* (2006.01)
*A61B 5/00* (2006.01)

(52) U.S. Cl.
CPC .......... *A61B 1/2275* (2013.01); *A61B 5/0053* (2013.01); *A61B 5/0075* (2013.01)

(58) Field of Classification Search
CPC .... A61B 1/2275; A61B 5/0075; A61B 5/0053
USPC .................................................. 600/473–480
See application file for complete search history.

(56) References Cited

U.S. PATENT DOCUMENTS

| | | | |
|---|---|---|---|
| 7,586,618 B2 | 9/2009 | Marks et al. | 356/451 |
| 7,623,908 B2 | 11/2009 | Boppart et al. | 600/477 |
| 7,725,169 B2 | 5/2010 | Boppart et al. | 600/473 |
| 7,787,129 B2 | 8/2010 | Zysk et al. | 356/481 |
| 8,115,934 B2 | 2/2012 | Boppart et al. | 356/479 |
| 2003/0082104 A1 | 5/2003 | Mertelmeier | 424/9.4 |
| 2004/0181128 A1 | 9/2004 | Masters | 600/200 |
| 2006/0276709 A1 | 12/2006 | Khamene et al. | 600/416 |

(Continued)

FOREIGN PATENT DOCUMENTS

WO    WO 02/088705 A2    11/2002    ............. G01N 33/00

OTHER PUBLICATIONS

American Academy of Family Physicians, "Otitis Media With Effusion," *Pediatrics*, vol. 113, No. 5, pp. 1412-1429 (May 2004).

(Continued)

*Primary Examiner* — Sanjay Cattungal
(74) *Attorney, Agent, or Firm* — Sunstein Kann Murphy & Timbers LLP

(57) ABSTRACT

Methods and apparatus for performing interferometric measurements on ear tissue within a person's ear, wherein the measurements are performed as a function of pressure within the ear canal. Measurements may be performed at a plurality of pressures, including pressures greater than, and less than, atmospheric pressure. Using an apparatus in accordance with the invention, methods are provided for characterizing a tympanic membrane, as well as a biofilm adjacent to the tympanic membrane, and an effusion in the middle ear. The tympanic membrane may be characterized as to geometrical features and mobility. Characterizations provided by the apparatus serve to diagnose ear pathology.

44 Claims, 6 Drawing Sheets

(56) References Cited

U.S. PATENT DOCUMENTS

| | | | | |
|---|---|---|---|---|
| 2009/0185191 | A1* | 7/2009 | Boppart | A61B 5/0066 356/479 |
| 2010/0094137 | A1* | 4/2010 | Furlong | A61B 1/042 600/477 |
| 2013/0060131 | A1* | 3/2013 | Oghalai | A61B 1/00165 600/425 |
| 2015/0351606 | A1* | 12/2015 | Ruppersberg | A61B 1/00179 600/200 |
| 2016/0007840 | A1* | 1/2016 | Boppart | A61B 5/0075 600/188 |

OTHER PUBLICATIONS

Hall-Stoodley et al., "Direct Detection of Bacterial Biofilms on the Middle-Ear Mucosa of Children with Chronic Otitis Media," *JAMA*, vol. 296, No. 2, pp. 202-211 (Jul. 2006).

Jung et al., "Handheld Optical Coherence Tomography Scanner for Primary Care Diagnostics," *IEEE T. Bio-Med. Eng.*, vol. 58, No. 3, pp. 741-744 (Mar. 2011).

Marks et al., "Inverse scattering for frequency-scanned full-field optical coherence tomography," *J. Opt. Soc. Am. A*, vol. 24, No. 4, pp. 1034-1041 (Apr. 2007).

Nguyen et al., "Noninvasive in vivo optical detection of biofilm in the human middle ear," *Proc. Nat. Acad. Sci.*, vol. 109, No. 24, pp. 9529-9534 (Jun. 2012).

Pitris et al., "High-Resolution Imaging of the Middle Ear with Optical Coherence Tomography: A Feasibility Study," *Arch. Otolaryngol.*, vol. 127, pp. 637-642 (Jun. 2001).

Reed et al., "Gradient-index fiber-optic microprobes for minimally invasive in vivo low-coherence interferometry," *Opt. Lett.*, vol. 27, No. 20, pp. 1794-1796 (Oct. 2002).

Shelton et al., "Optical coherence tomography for advanced screening in the primary care office," *J. Biophotonics*, pp. 1-9, (Apr. 2013).

Takata et al., "Evidence Assessment of the Accuracy of Methods of Diagnosing Middle Ear Effusion in Children with Otitis Media with Effusion," *Pediatrics*, vol. 112, No. 6, pp. 1379-1387 (Dec. 2003).

Xi et al., "High-resolution three-dimensional imaging of biofilm development using optical coherence tomography," *J. Biomed. Opt.*, vol. 11, No. 3, pp. 134001-1-134001-6 (May/Jun. 2006).

Zysk et al., "Computational methods of analysis of human breast tumor tissue in optical coherence tomography images," *J. Biomed. Opt.*, vol. 11, No. 5, pp. 054015-1-054015-7 (Sep./Oct. 2006).

Heine Beta® 200 Fiber Optic Otoscope, 1 page.

Welch Allyn Macro View™ sell sheet, 2 pages (2008).

\* cited by examiner

QUANTITATIVE PNEUMATIC OTOSCOPY USING COHERENT LIGHT RANGING TECHNIQUES

The present application claims priority of U.S. Provisional Patent Application Ser. No. 61/869,805, filed Aug. 26, 2013, and incorporated herein by reference.

This invention was made with government support under Grant R01 EB013723, awarded by the National Institutes of Health. The Government has certain rights in the invention.

TECHNICAL FIELD

The present invention relates to apparatus and methods for imaging otoscopy, and, more particularly, to apparatus and methods for three-dimensional imaging of ear tissue under conditions of controlled pressure in the ear canal.

BACKGROUND ART

Low-coherence interferometry (LCI) is a well-known optical coherence technique capable of measuring one-dimensional depth-resolved tissue structure with a typical resolution of several microns. Optical Coherence Tomography (OCT) combines LCI with a lateral scanning mechanism to generate cross-sectional images of biological tissues. LCI and OCT are non-invasive imaging techniques, typically using near-infrared light to obtain structural information from human tissues in vivo. The use of OCT for non-invasively imaging ear tissue was taught in U.S. Pat. No. 8,115,934 (hereinafter "Boppart '934," entitled "Device and Method for Imaging the Ear using Optical Coherence Tomography," and incorporated herein by reference. Further information regarding the application of OCT to imaging ear tissue may be found in the following references, all of which are incorporated herein by reference:

Xi et al., "High-resolution three-dimensional imaging of biofilm development using optical coherence tomography," *J. Biomed. Opt.*, vol. 11, pp. 11(3):134001-1-134001-6, (2006).

Pitris et al., "High-resolution imaging of the middle ear with optical coherence tomography: a feasibility study," *Arch. Otolaryngology—Head & Neck Surg.*, vol. 127, pp. 637-642, (2001).

Jung et al., "Handheld Optical Coherence Tomography Scanner for Primary Care Diagnostics," *IEEE Trans. Biomed. Eng.*, vol. 58, pp. 741-44, (2011).

Nguyen et al., "Noninvasive in vivo optical detection of biofilm in the human middle ear," *Proc. Nat. Acad. Of Sciences*, vol. 109, pp. 9529-34, (May 29, 2012), ("Nguyen 2012").

Shelton et al., "Optical coherence tomography for advanced screening in the primary care office," *J. Biophotonics*, DOI: 10.1002/jbio.0.201200243, (Apr. 18, 2013).

In the prior art, biofilms were imaged in controlled environments, such as within a flow-cell. Two-dimensional and three-dimensional OCT images were shown in Nguyen 2012. Each 2-D image in Nguyen was composed of a series of adjacent 1-D LCI depth scans. Sufficient information exists in the 1-D depth scans to determine the thickness and optical properties of layered structures, such as the layered biofilm on the tympanic membrane.

Various diagnostic applications call, not only for otoscopy in general, but for use of a pneumatic otoscope in particular, for visualizing the ear canal, tympanic membrane, and middle-ear, to detect and diagnose ear diseases such as otitis media (OM) or otitis media with effusion (OME). In pneumatic otoscopy, a special tip is used that effectively seals the ear canal, forming a closed pressure system in the ear. Pneumatic otoscopes are typically equipped with an insufflation bulb connected to the otoscope via a tube, allowing the pressure inside the ear canal to be modulated. These pressure changes cause the thin eardrum to deflect or retract, depending on whether the applied pressure is positive or negative. The amount of deflection gives the physician some indication of the mechanical stiffness of the eardrum. The degree of mechanical stiffness of the eardrum is an indication of whether the eardrum is infected. Additionally, if an effusion (fluid) exists in the middle ear, the eardrum is less mobile than in the case of a healthy ear.

Other than pneumatic otoscopy, there are mainly two in vivo diagnostic methods for identifying middle-ear pathologies. Tympanometry measures sound energy transmission/reflection (i.e., compliance/mobility) of the tympanic membrane by recording a tympanogram in response to air pressure changes inside the ear canal. Tympanograms are classified as type A (normal), type B (indicating middle-ear effusion) or type C (indicating Eustachian tube dysfunction). Acoustic reflectometry measures the acoustic reflectivity spectrum of the middle-ear in response to an incident sound. The curve of the spectrum is used to characterize the extent of OME. Comprehensive evidence assessment on the accuracy (sensitivity and specificity) of the three methods reveals that pneumatic otoscopy has better performance than the two acoustic methods. Moreover, pneumatic otoscopy is more cost-effective and easier to use. Thus, the 2004 clinical practice guideline on OME from the American Academy of Pediatrics has recommended that clinicians use pneumatic otoscopy as the primary diagnostic method. In this respect, all efforts to improve the validity and reliability of pneumatic otoscopy are warranted.

Otoscopy based on pneumatic otoscopes is currently the primary diagnostic tool for various ear pathologies. However, the diagnostic process is currently more subjective than objective, more of an art than a science. One of the biggest problems with current pneumatic otoscopes is that they require a lot of user experience to be effective. Studies have shown that less than half of pneumatic otoscope exams are correctly diagnosed, largely because the measurement is so subjective. Physicians must estimate how mobile the eardrum is by looking at a two-dimensional (2D) image in a plane perpendicular to the axis of motion. Trained eyes are required to decipher a wide variety of tympanic membrane and middle-ear images, some of which are empirically linked to various disease states. Treatments that follow such subjective diagnosis rely on the individual judgments of physicians. Currently, few objective tests are available to assess the significance of disease, and limitations are more evident in the primary care or general pediatrician's office, remote from access to specialists in otolaryngology.

Furthermore, evaluation and monitoring of treatments (such as antibiotic treatments in OM or OME) in patients is often difficult, because quantitative measures are lacking. All these limitations can be ultimately attributed to the qualitative nature of the information acquired, and flow from the fact that a prior art pneumatic otoscope is basically a low-magnification microscopy-type of instrument.

A prior art LCI/OCT otoscope is shown schematically in FIG. 1A, which appears as FIG. 10 in the Boppart '934 patent. As described there, a device 400 for imaging the ear using optical coherence tomography is provided which includes a core imaging unit 410 in communication with a core software unit 430. Preferably, the core imaging unit 410 is not only in communication with, but also integrated within, the device 400 so as to provide a compact portable instrument which allows straightforward clinical operation in an office-based setting. The core imaging unit 410 is in communication with the core software unit 430, as shown in FIG. 1B. If the core imaging unit 410 is integrated within the device 400, then the core software unit can communicate directly with the device 400.

The device 400 can image visible structures (i.e. structures that can be seen with the naked eye) such, as the tympanic membrane, with enough accuracy to account for slight variations or movement in those structures. For example, device 400 can image variations or movement of the tympanic membrane. Additionally, the device 400 can image structures which are not visible to the naked eye, such as middle ear structures behind the tympanic membrane in order to search for tissue, such as biofilms.

In accordance with the operation of LCI or OCT devices, light emitted by a low-coherence source 402 is incident upon ear tissue via otoscope 401, and is combined with a reference beam, such as derived via reference mirror 424, in interferometer 408, thereby gating a detection signal to a tightly localized scattering window. The reference beam may share a common path with the signal beam and be reflected, for example, from a window in the signal beam path. Low-coherence source 402 may be swept in wavelength, and the interferometer output may be wavelength-resolved by spectrometer 412.

The device 400 includes any imaging device which can non-invasively image the middle ear, direct and receive light from the middle ear and send the received light to the core imaging unit 410. Preferably, the imaging device 400 also includes any device which can form a direct line of sight from the tympanic membrane to the outside of the ear, such as an ear speculum. The imaging device 400 includes things such as an otoscope 401, a pneumatic otoscope, ear plugs, ear speculums, and other such devices. In one embodiment, the otoscope 401 is a pneumatic otoscope, such as the MacroView™ otoscope manufactured by Welch Allyn Inc. of Skaneateles Falls, N.Y., or the BETA 200 otoscope manufactured by HEINE Optotechnik of Germany.

Preferably, the imaging device 400 is adapted for selecting and analyzing tissue in the patient's middle ear. This means that the device is capable of non-invasively imaging inside the patient's ear canal and more specifically, non-invasively imaging the patient's middle ear. Preferably, at least a portion of the device is adapted for insertion into the patient's ear canal, allowing for non-invasive imaging of the patient's ear canal and or middle ear. In one embodiment, at least a portion of the device 400 has a diameter or width which does not exceed 1 cm and preferably does not exceed 0.5 cm, so that the device 400 can be inserted into an ear. However, since animal ears can be much larger than human ears, at least a portion of device 400 can be adapted for insertion into those ears and made much larger so as to fit within the ear canal of any animal, large or small.

In one embodiment, the device 400 includes a fiber based device 406 connected with or integrated with the otoscope 401, as shown in FIG. 1B. The fiber based device 406 includes any device which can act as a light guide and carry beams of light from one place to another. Preferably, the fiber based device 406 includes a fiber optic cable. When the otoscope 401 is placed near or within a patient's ear canal 442, light from the inner or middle-ear 444 carried through the fiber based device 406 to the core imaging unit 410. The fiber based device 406 is connected with the otoscope 401. In one embodiment, the fiber based device 406 delivers light into the optical system of the otoscope 401, and uses the existing or modified optics of the otoscope 401 to also direct a near-infrared beam to the middle-ear.

In one embodiment, the fiber based device is attached to an outside surface of the otoscope 401. In one embodiment, the fiber based device 406 is run through at least a portion of the otoscope 401, as shown in FIG. 1B. Preferably, the fiber based device 406 is run through at least portions of the head unit 402 and the ear speculum 404 (otherwise referred to herein as a tip of the otoscope 401). More preferably, the fiber based device 406 is run through the ear speculum 404 and positioned to receive light which enters the ear speculum 404. The ear speculum 404 provides mechanical support for the fiber based device 406 to perpendicularly approach an eardrum 446 to within about 5 mm, enabling non-invasive in-vivo ear diagnosis simultaneously with a regular otoscope exam.

The fiber based device 406 is preferably miniaturized to avoid blocking the field of the view of the otoscope 401, which is approximately 2.5 mm in diameter in some cases. Additionally, it is preferable that the fiber based device 406 be flexible enough to adapt to the curved shape of the ear speculum 404. Because of the dual role played by the fiber based device 406 as an optical source and receiver, the fiber based device 406 should produce a collimated beam or a weakly focused beam with a focus approximately the distance D between a tip 411 of the ear speculum 404 and the eardrum (~3-5 mm). A divergent beam will deteriorate the collection efficiency of the back-reflected optical signal. These requirements are achieved by fusion-splicing a gradient index (GRIN) fiber (which acts as a focusing element) onto the end of a single mode fiber (SMF) connected to the sample arm of the LCI interferometer. The GRIN fiber lens face is then polished to attain the appropriate angle and total GRIN fiber length.

In one embodiment, the device 400 is configured with a miniature video camera 409, and real-time video of the ear canal and/or eardrum 446 from the device 400 is used to do a wide-field survey, as well as to select or track the location in the ear on the eardrum where an OCT measurement is acquired. The video camera 409 is preferably connected with the ear speculum 404.

In one embodiment, the fiber based device 406 includes a fiber-optic OCT probe which can be used to generate OCT signals, LCI signals, or both OCT and LCI signals. In one embodiment, the location in the inner or middle-ear 444 on an eardrum 446 where an OCT signal is acquired by the device 400 is illuminated, preferably by guiding light through the fiber based device 406 and onto the eardrum 446 in order to collect an OCT signal. The illumination is a low-power (1 mW) NIR beam which does not affect the regular operations of the otoscope 401. The back-reflected NIR beam from the middle-ear tissues is collected by the same fiber based device 406 and used to infer the depth-resolved structures of tissue within the ear 438, and specifically tissue within the inner or middle-ear 444.

In one embodiment, in order to obtain OCT data, more than one OCT signal is acquired. The OCT signals are acquired at high speeds (>250 Hz). This enables rapid collection of large depth-resolved datasets for analysis, as well as tracking of the movement of middle-ear structures (e.g., the eardrum) due to pneumatic operation of the otoscope 401, which can be monitored in real time. The simultaneous capture of a video image of the NIR beam on the eardrum, along with the depth-resolved OCT signals, enables correlation of suspect visual findings with depth-resolved measurements and the generation of OCT data.

In one embodiment, in order to obtain OCT data, an LCI signal is generated which retrieves a depth-resolved reflectance profile at the location of the probing beam and along an axial direction 440 of the fiber based device 406 (axis-scan). The resulting OCT data generated represents one-dimensional structural scattering information of the tissue being measured, such as inner or middle-ear tissue. Since the LCI signal in this case is fast, relative to small lateral movements between the ear speculum 404 and the ear 438, multiple axial-scans can be acquired rapidly, corresponding to a specific set of sampling data that can be analyzed by a computer using the core software unit 430 or reconstructed to produce a cross-section type of "image" associated with the continuous trace of these sampled regions. The resulting OCT data facilitates the detection of tissue structures including the eardrum 446, ossicles 448, and the presence of a bio film. In one embodiment, a traditional spectral-domain LCI system can be used as the core imaging unit 410 in order to generate an LCI signal and obtain OCT data.

All of the foregoing is known in the art, and has been described in the Boppart '934 patent.

It would be highly desirable, however, to provide physicians with direct access to the axis of motion of the eardrum (i.e., the axis of the ear canal), in a quantitative manner, and in relation to a known pressure in the ear canal. Additionally, it would also be highly desirable to provide micron-scale resolution for precise, quantitative measurements of eardrum motion under known pressure conditions. It would be still more useful that physicians retain access to 2D surface images to which they are accustomed. A device that could provide such functionality would be very beneficial.

SUMMARY OF EMBODIMENTS OF THE INVENTION

In accordance with embodiments of the invention, a system is provided for pneumatic otoscopic imaging. The system has a source of light and a hand-held otoscope for abutment with an ear canal for directing the light to ear tissue and for collecting scattered light from the ear tissue. The system also has an interferometer for combining the scattered light from the ear tissue with a reference beam for generating an interferometry signal, a pneumatic port coupled to the hand-held otoscope for governing a pressure within the ear canal, a pump for varying the pressure within the ear canal and for generating a pressure signal, and a processor for receiving the interferometry signal and the pressure signal and for generating therefrom a quantitative characterization of the ear tissue under a specified condition of pressure within the ear canal.

In accordance with alternate embodiments of the present invention, the pneumatic otoscopic imaging system may also have a controller for modulating a pressure at the pneumatic port and thus the pressure within the ear canal. The pressure within the ear canal may exceed atmospheric pressure, or vice versa. The controller may include an insufflation bulb as well as an automated controller. The controller may include a pneumatic piston or an acoustic transducer. The source of light may be a source of low-coherence light, and may be characterized by a central wavelength swept as a function of time. The reference beam may be derived from the source of light, and, more particularly, may be derived from a reflection within a path traversed by the light en route from the source to the ear tissue.

In other embodiments of the invention, the system may have an optical fiber for coupling light from the source of low-coherence light to the hand-held otoscope. The source of light may be a superluminescent diode, and may include an infrared component or a near-infrared component. The source of light may be disposed within a core imaging unit, as may the interferometer, as well.

In yet other embodiments of the invention, the system may also have a camera for imaging scattering from a surface of the ear canal, and/or the tympanic membrane, as well as a pressure sensor for measuring instantaneous pressure within the ear canal, and an accelerometer for tracking relative motion between the hand-held otoscope and the ear tissue.

In accordance with another aspect of the present invention, a hand-held pneumatic otoscope is provided. The hand-held pneumatic otoscope has an otoscopic tip for insertion into an ear canal, and focusing optics for directing light to ear tissue via the ear canal and for collecting scattered light from the ear tissue. The hand-held pneumatic otoscope also has a pneumatic port for modulating a pressure within the ear canal, a pressure sensor for measuring the pressure within the ear canal and for generating a pressure signal, and an optical coupler for directing the scattered light to an interferometer for interfering the scattered light from the ear tissue with a reference beam to generate an interference signal under a specified condition of pressure within the ear canal.

In further embodiments of the invention, light is coupled from a source remote with respect to the hand-held pneumatic otoscope, such as via an optical fiber. The hand-held pneumatic otoscope may also have a pressure sensor adapted for measuring air pressure in the ear canal, and a controller for modulating pressure in the ear canal. The controller may be an automated controller for modulating pressure in the ear canal, or may be an insufflation bulb for manually modulating pressure in the ear canal, to name two examples.

The hand-held pneumatic otoscope may also have a pump for modulating pressure in the ear canal, and a camera for imaging scattering from a surface of the ear canal and/or the tympanic membrane.

In accordance with another aspect of the present invention, a method is provided for characterizing a tympanic membrane of a person. The method has steps of:
  a. illuminating the tympanic membrane of an ear of a person with a broadband optical beam, the ear of the person having an ear canal;
  b. interfering light scattered by the tympanic membrane with a reference beam for generating an interferometric signal;
  c. varying pressure within the ear canal; and
  d. deriving a derivative of a displacement, with respect to pressure within the ear canal, of a position on the tympanic membrane relative to a fiducial position.

In other embodiments, there may be additional steps of mapping the distensibility in three dimensions across and through the tympanic membrane, or diagnosing movement of ossicles based in tympanic membrane response to sound waves.

In yet another aspect of the present invention, a method is provided for characterizing at least one of biofilm adjacent to a tympanic membrane of a person and an effusion in a middle ear of the person. The method has steps of:
  a. illuminating the tympanic membrane of an ear of a person with a broadband optical beam, the ear of the person having an ear canal;
  b. interfering light scattered by the tympanic membrane with a reference beam for generating an interferometric signal;
  c. varying pressure within the ear canal; and d. ascertaining a specified parameter of any biofilm adjacent to the tympanic membrane and any effusion within the middle ear of the person on the basis of the interferometric signal at more than a single value of the pressure within the ear canal.

In further embodiments, the specified parameter may be a measure of geometrical thickness of the biofilm, or a measure of viscosity. The method may include a further step of diagnosing an ear pathology based on the specified parameter, and the ear pathology may be chronic otitis media.

In a further embodiment yet, a method is provided for measuring mobility of a tympanic membrane of a person. The method has steps of:

a. illuminating the tympanic membrane with a broadband optical beam via an ear canal of the person;
b. interfering light scattered by the tympanic membrane with a reference beam derived from the broadband optical beam to generate an interferometric signal;
c. modulating an air pressure internal to the ear canal;
d. quantifying a geometrical characteristic of the tympanic membrane as a function of air pressure in the ear canal based on the interferometric signal; and
e. deriving tympanic membrane mobility based on the quantified geometrical characteristic.

Alternatively, the geometrical characteristic may be a displacement relative to a fiducial reference surface, or a bulging of the tympanic membrane. Other steps may include ascertaining a specified parameter of any biofilm adjacent to the tympanic membrane on the basis of the interferometric signal, and diagnosing an ear pathology based on the specified parameter. The ear pathology may be otitis media. Finally, there may also be steps of ascertaining a specified parameter of any middle ear effusion on the basis of the interferometric signal, and diagnosing an ear pathology based on the specified parameter.

BRIEF DESCRIPTION OF THE DRAWINGS

The foregoing features of the invention will be more readily understood by reference to the following detailed description, taken with reference to the accompanying drawings, in which:

FIG. 1A shows a schematic diagram of salient components of the optical system of an LCI otoscope, while

DETAILED DESCRIPTION OF EMBODIMENTS OF THE INVENTION

Figure 1A:
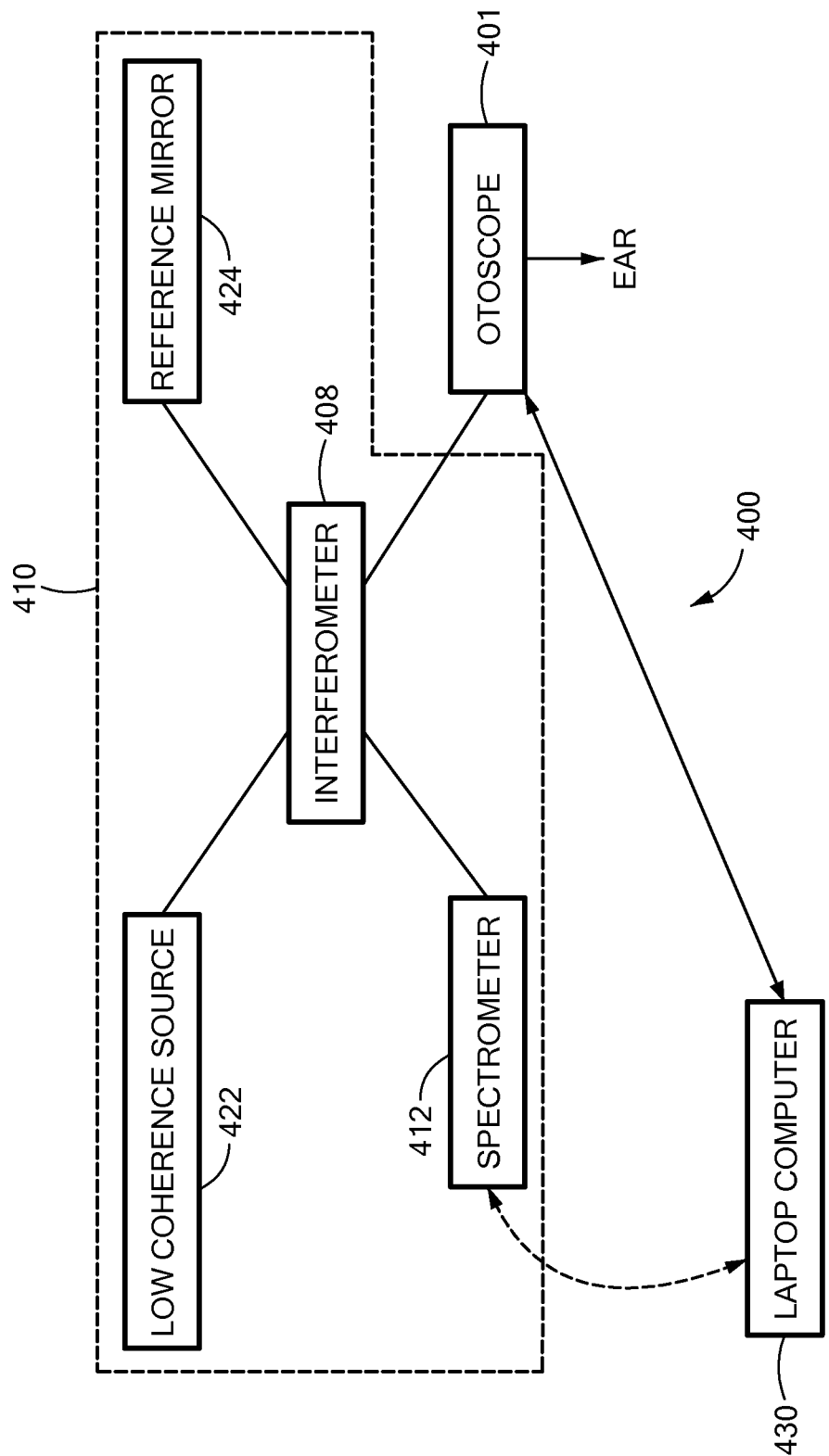

Definitions: The term "image" shall refer to any multidimensional representation, whether in tangible or otherwise perceptible form, or otherwise, whereby a value of some characteristic (amplitude, phase, etc.) is associated with each of a plurality of locations corresponding to dimensional coordinates of an object in physical space, though not necessarily mapped one-to-one thereon. Thus, for example, the graphic display of the spatial distribution of some field, either scalar or vectorial, such as brightness or color, constitutes an image. So, also, does an array of numbers, such as a 3D holographic dataset, in a computer memory or holographic medium. Similarly, "imaging" refers to the rendering of a stated physical characteristic in terms of one or more images.

The terms "object," "sample," and "specimen" shall refer, interchangeably, to a tangible, non-transitory physical object capable of being rendered as an image.

When used to modify terms such as "beam," "pulse," etc., the terms "sample" and "signal" are used herein interchangeably.

The term "scattering medium," as used herein and in any appended claim, shall mean a medium in which an incident electromagnetic wave, of a wavelength range pertinent to the context under discussion, shall be characterized by a mean free path to scatter that is substantially shorter than the dimension of the medium in the propagation direction of the incident electromagnetic wave.

The term "scattering biological tissue," as used herein and in any appended claim, shall mean an organized ensemble of interconnected cells of an organism that has the optical properties associated with a scattering medium, as defined above.

The term "low-coherence" (or "broadband," as used interchangeably herein) applies to a source of illumination for which the coherence length is shorter than 30 μm, and/or for which $\Delta k/k_0$ is at least 10%, with $k_0$ denoting the central wavenumber of the spectrum illuminating the sample, while $\Delta k$ denotes the range of illuminating wavenumbers. It is to be understood that, within the scope of the present invention, the wavelength of the source need not be fixed in time, indeed, the wavelength of the source may be swept in time.

The term "controller," as used herein, shall mean any instrument that holds a process or condition at a desired level, whether manually, or in a preprogrammed manner.

As used herein, "LCI/OCT" shall denote "either LCI or OCT."

The term "pump," as used herein and in any appended claims, shall refer to any device known in the art that varies the pressure of gas in a specified volume. Thus, a pump may increase the pressure in a specified volume, by conveying gas from outside the volume (or by decreasing the volume, etc.), and may also give rise to a lower pressure, as by extracting gas from the specified volume. Examples of a "pump," as the term is used herein, include a bellows or a syringe device, in which gas may be moved into, or out of, a reservoir, or ballast, of variable volume into a specified region, resulting in increased or decreased pressure within the specified volume. As another particular example, an acoustic transducer that launches an acoustic wave, thereby modulating pressure within the ear canal of a person is considered to be a "pump," within the scope of the present invention.

In accordance with embodiments of the present invention described in detail herein, an LCI/OCT modality is integrated into a pneumatic otoscope in such a manner as to provide quantitative measures that may be used to monitor the health status of ears and to guide appropriate treatment and therapy. The capacity of the LCI/OCT modality to provide quantitative (i.e., depth-resolved) structural characterization, for example, compliments pneumatic otoscopy for enhanced diagnostic ability. This quantification not only provides quantitative data on the status of ear health and disease, hitherto unavailable, but also provides repeated monitoring for following disease progression or regression following medical treatments.

Additionally, a pneumatic otoscope instrument, as described herein, may advantageously augment LCI/OCT by allowing an LCI/OCT probe to gain access to the ear anatomy, and by facilitating the tracking of the position where an LCI/OCT measurement is being acquired. Hence, embodiments of the present invention permit not only the standard qualitative visualization and video capture of the ear anatomy and pathology, but also simultaneous LCI/OCT quantification of tympanic membrane position and integrity, middle-ear anatomy, and the presence and classification of middle ear effusions.

Additionally, as described in detail below, a pressure sensor is be integrated into an otoscope tip to measure the pressure in the ear canal while LCI/OCT quantification is being performed. Knowing the pressure change, as well as the resulting displacement of the eardrum allows for quantitative analysis of the mechanical properties of the eardrum.

Integration of the LCI/OCT modality capable of quantitative (i.e., depth-resolved) structural characterization, as described in detail in the following discussion, compliments pneumatic otoscopy for enhanced diagnostic ability. This quantification not only can provide quantitative data on the status of ear health and disease, but also provide repeated monitoring for following disease progression or regression following medical treatments. In addition, the pneumatic otoscope instrument augments LCI/OCT by allowing the LCI/OCT probe to gain access to the ear anatomy, and to facilitate tracking of the position where the LCI/OCT measurement is being acquired. Hence, this invention permits not only the standard qualitative visualization and video capture of the ear anatomy and pathology, but also simultaneous LCI/OCT quantification of tympanic membrane position and integrity, middle-ear anatomy, and the presence and classification of middle ear effusions.

Three important applications for the aforesaid capability may be enumerated by way of example:

A. Discriminating Chronic OM as Against Non-Chronic OM in Order to Avoid Unnecessary Medical or Surgical Interventions OM (with or without effusion) is the most common pediatric infectious illness, affecting approximately 50% of the pediatric population, It is usually of no concern except that it may become chronic. Chronic OM occurs at a much lower percentage, but can delay speech development and result in hearing loss in later life. Unfortunately, chronic and non-chronic OM produce similar otoscopic findings. Recent clinical studies have established the one-to-one correspondence between chronic OM and the presence of biofilms (i.e., aggregated bacterial colony within an extracellular matrix) behind the tympanic membrane (i.e., eardrum) and within the middle ear. Thus, the presence of a biofilm can be treated as the "structural signature" of chronic OM. Due to its thin film (typically 10-100 um), biofilms have little optical contrast when viewed with the human eye through an otoscope, and can rarely be distinguished from the surrounding ear tissues, In contrast, it has been demonstrated (and discussed in Nguyen 2012) that biofilms can readily be detected and quantified by LCI/OCT through a mechanism analogous to how pulse-echo ultrasound locates material density boundaries within thick tissues, i.e., the coherence ranging mechanism.

B. Quantifying Properties of the Tympanic Membrane

The mobility of the tympanic membrane (eardrum) in response to the pressure changes inside the ear (pneumatic pressure) is of important diagnostic value in pneumatic otoscopy. The retarded mobility indicates the presence of a fluid (effusion) in the middle-ear, which is diagnosed as OM with effusion (OME). However, the degree of mobility is usually graded in qualitative terms. The depth-resolved detection and range-finding ability of LCI/OCT easily quantifies this mobility, i.e., the extent of OME, as well as the optical scattering or turbidity of the effusion itself, within the middle ear. The quantification is most useful when the buildup or clearance of the effusion must be monitored to study the pathological origin of OME and to evaluate corresponding treatments. As another example, the shape of the tympanic membrane can be used to differentiate acute OM (resulting in a bulging eardrum) from OME (resulting in a retracted eardrum position). Antibiotic treatment is efficient in the former case but inefficient in the latter case. The degree of bulging or retraction can be easily quantified by an LCI/OCT-enabled otoscope.

The slope of the curve representing canal pressure (x-axis) vs. tympanic membrane displacement (y-axis) may be referred to as the "distensibility" of the ear drum. The slope may be the derivative of the displacement vs. pressure at a particular pressure, or a measure defined over a range of pressures. Ear drum distensibility is often indicative of pathology, thereby serving advantageously as a biomarker. Quantification of ear drum distensibility in a clinical context is uniquely provided by the present invention.

Distensibility of the tympanic membrane may be mapped, using methods of the present invention, in three dimensions, across and through the tympanic membrane. Moreover, If positioning of the LCI/OCT beam over the malleus region of the tympanic membrane provides a measure of distensibility that is indicative of movement of the ossicles, which is diagnostic as well.

C. Obtaining Diagnostic Information Even in the Case where the Eardrum is Visually Opaque.

In many situations, the visibility of the tympanic membrane and middle-ear contents is impaired (due to tympanic membrane perforation, vascularity, cholesteatoma, tympanosclerosis, etc.), which compromises the diagnostic ability of pneumatic otoscopy. While the visible light employed in pneumatic otoscopy cannot penetrate the eardrum and visualization is only based on surface features, the near-infrared (NIR) light afforded by LCI/OCT has adequate penetration depth to access the middle-ear structures behind the eardrum. For example, the detection of a large amount of middle-ear effusion behind an opaque eardrum can be diagnosed as OME rather than a disease associated with the eardrum itself. The visible (surface features) and NIR (depth-resolved) tests used in conjunction provide a significant advantage to obtain more diagnostic information.

Thus, the enhanced pneumatic otoscope with coherence ranging capability may be advantageously used as a powerful, portable, office-based, diagnostic, monitoring, and research tool to detect, diagnosis, monitor, and improve our understanding of ear pathology. This better understanding will extend the applications of this device beyond those discussed above, and, in other embodiments of the invention, may comprise a cost-effective and efficient screening tool to identify patients in whom appropriate interventions must be initiated.

Figure 1B:
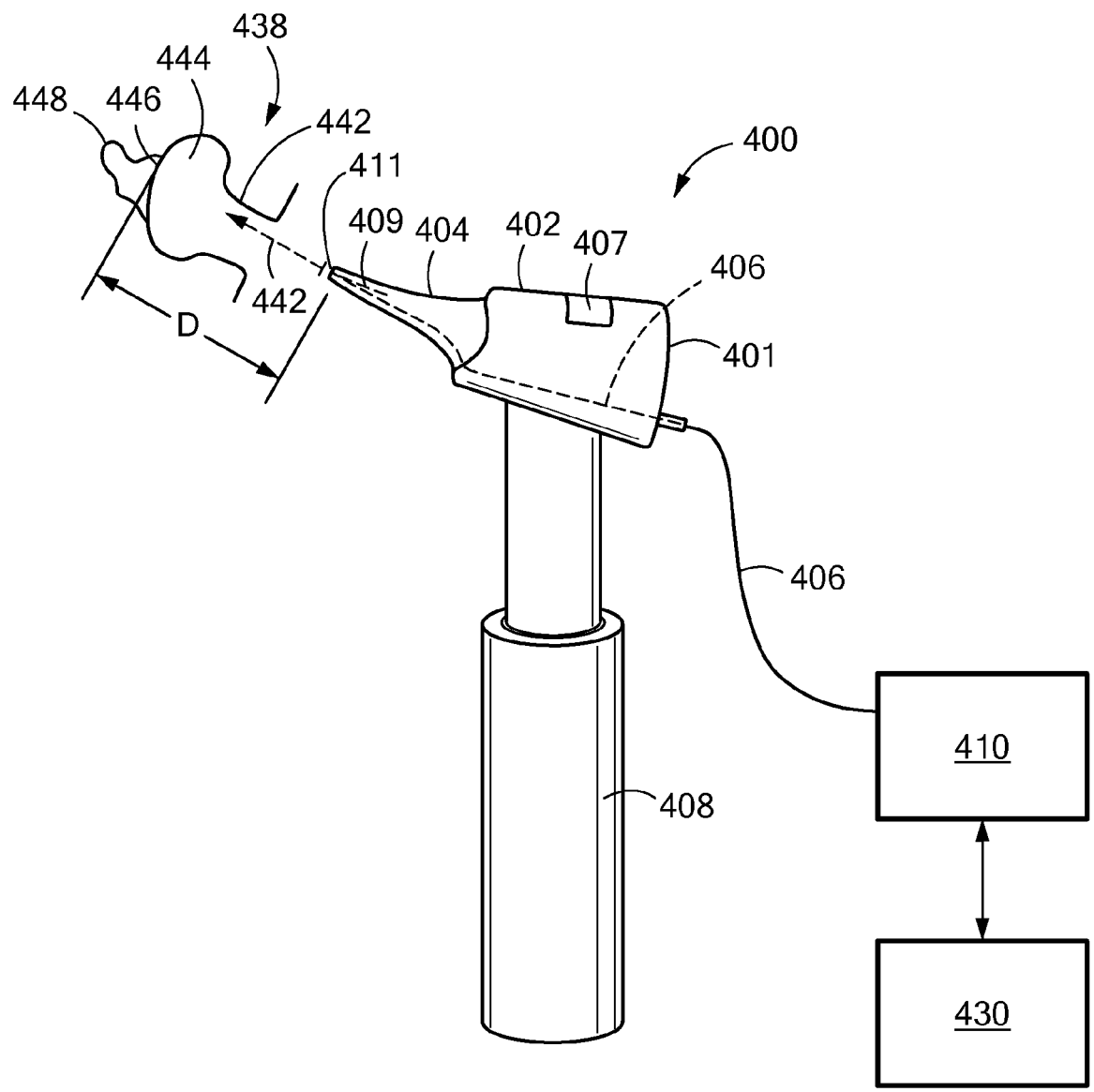
FIG. 1B depicts a prior art device for imaging the middle ear using OCT.
Figure 2:
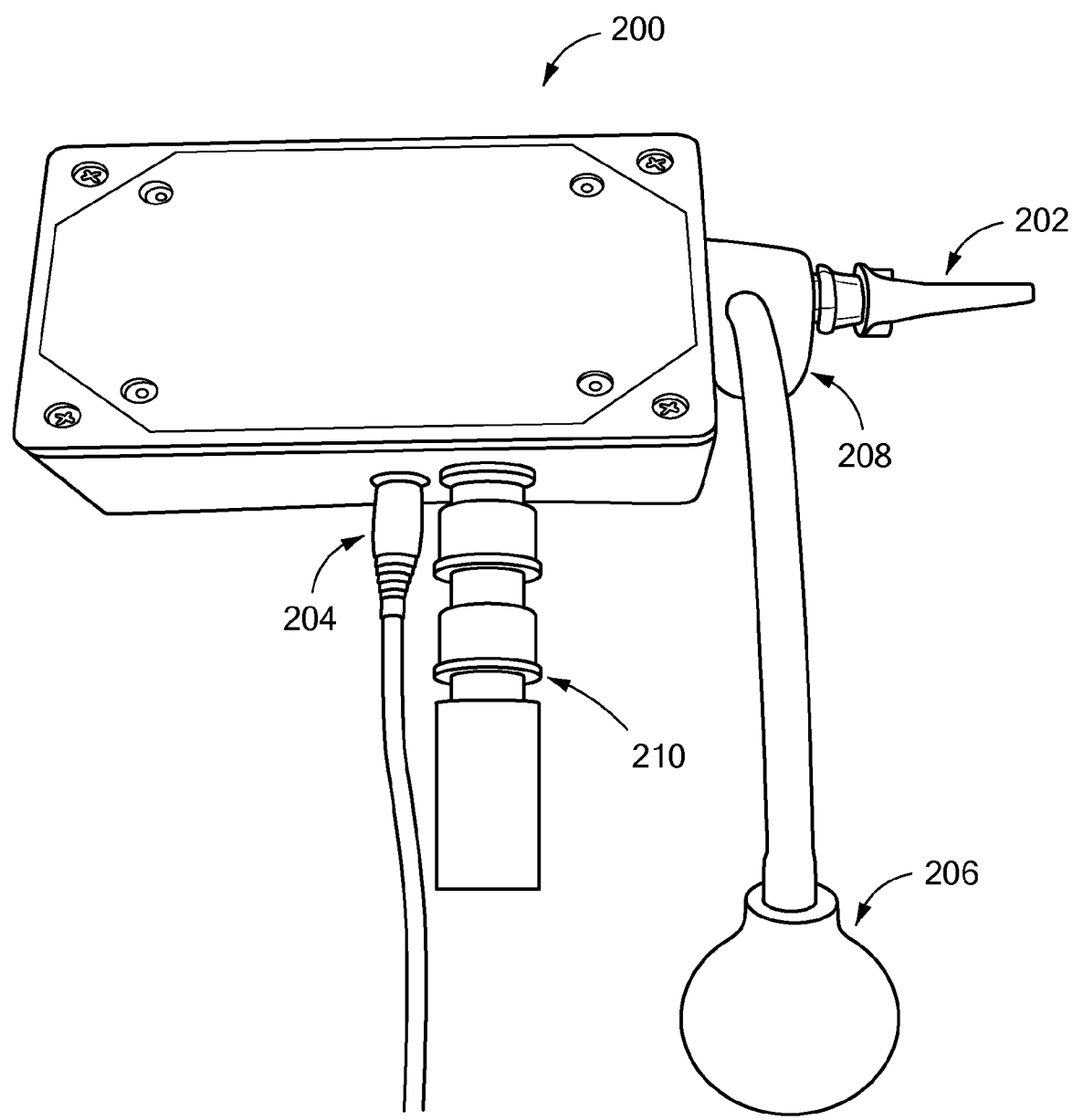
FIG. 2 shows component parts of a pneumatic LCI otoscope in accordance with an embodiment of the present invention.

An underlying platform for this technology, the handheld LCI/OCT otoscope, has been extensively described in the Background Section above, and in the Boppart '934 patent, to which the reader may turn for additional detail. A quantitative pneumatic extension of the otoscope described above with reference to FIGS. 1A and 1B is shown in FIG. 2, and designated there generally by numeral 200. In the system, a pneumatic seal is formed between the otoscope tip 404 and the ear canal 442 by means of sealing otoscope tip 202. The LCI/OCT beam conveyed from a broadband source (not shown) via optical fiber 204 is then shone on the eardrum while the pressure inside the ear canal is changed. The pressure inside the ear canal can be changed by a pump, which includes either via a manual insufflation bulb 206, or a small regulated, computer-controlled air pump, both of which can apply either a static pressure (stepping up or down) or a cyclical dynamic pressure waveform via pneumatic port 208. A computer controller is an example of a controller that may be used to control the pressure pump within the scope of the present invention. Pressure may be measured using any suitable pressure sensor (not shown) such as a piezoresistive solid state MEMS sensor, however any pressure sensor may be used within the scope of the present invention. A pressure signal is derived from the pressure sensor, or else from the controller that controls the pressure pump. Through the LCI/OCT imaging, the exact displacement of the eardrum may be measured, and displacement versus applied pressure plots can be generated and used for diagnostic purposes.

In preferred embodiments of the invention, LCI/OCT measurements are acquired at high speeds (where "high," in this context, designates a frequency exceeding 250 Hz). This enables rapid collection of large depth-resolved datasets for analysis, as well as tracking of the movement of middle-ear structures (e.g., the eardrum) due to pneumatic operation of the otoscope, which movement can be monitored in real time. Simultaneous capture of the video image of the NIR beam on the eardrum by a camera and associated optics designated generally by numeral 210, along with the depth-resolved LCI/OCT data, enables correlation of suspect visual findings with depth-resolved measurements.

Figure 3:
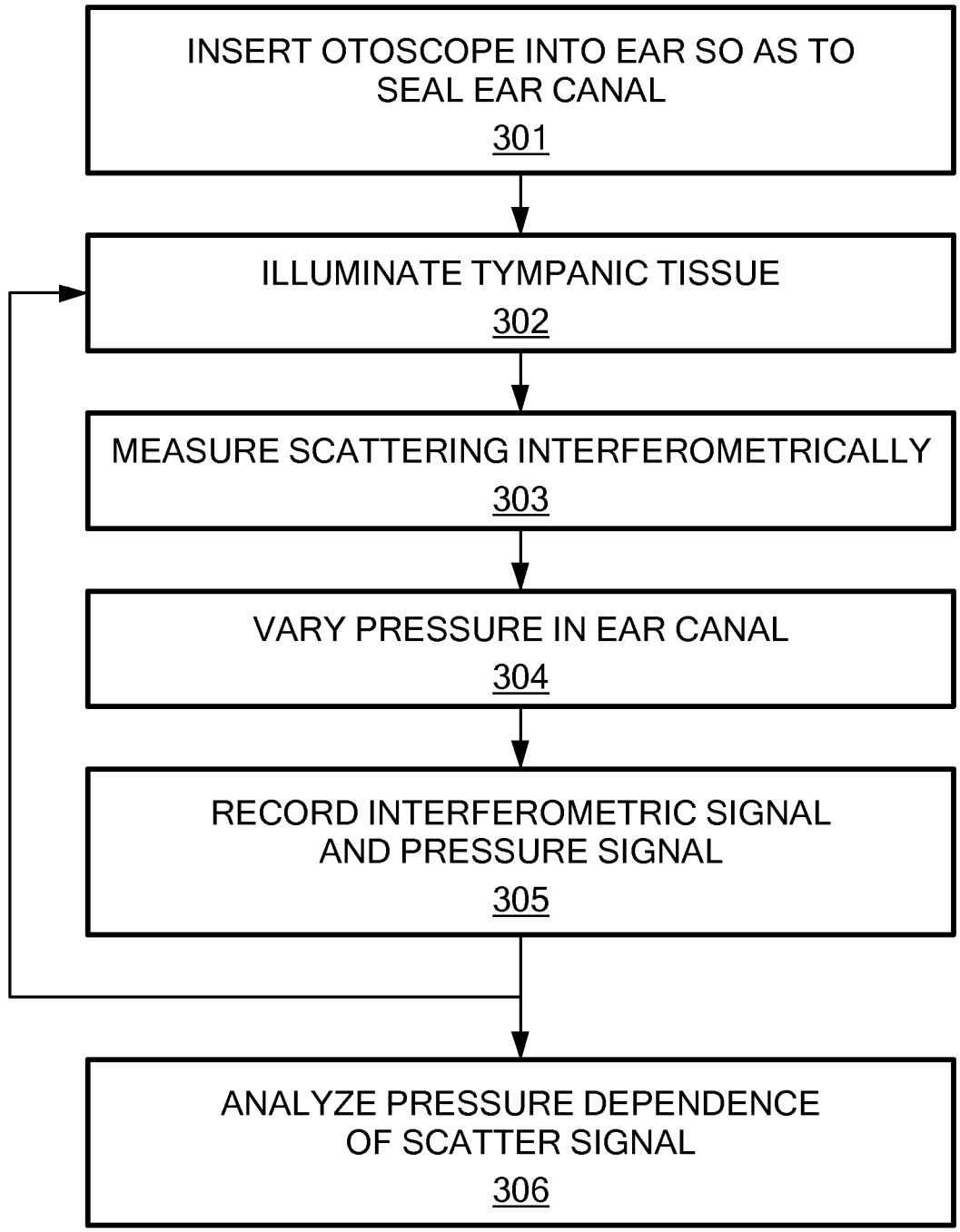
FIG. 3 is a flowchart depicting a modality for measurement of a specified parameter associated with an ear of a person.
Figure 4A:
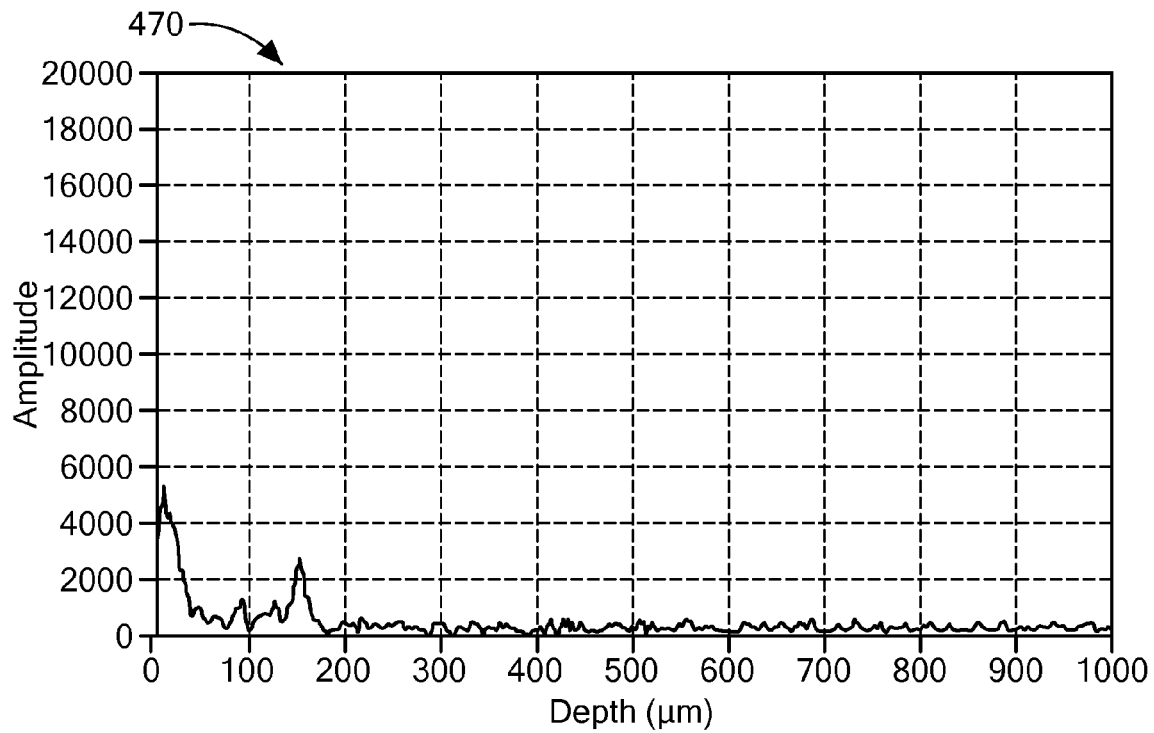
FIGS. 4A-4D are LCI depth scans of an eardrum at increasing pressure inside the ear canal.
Figure 4B:
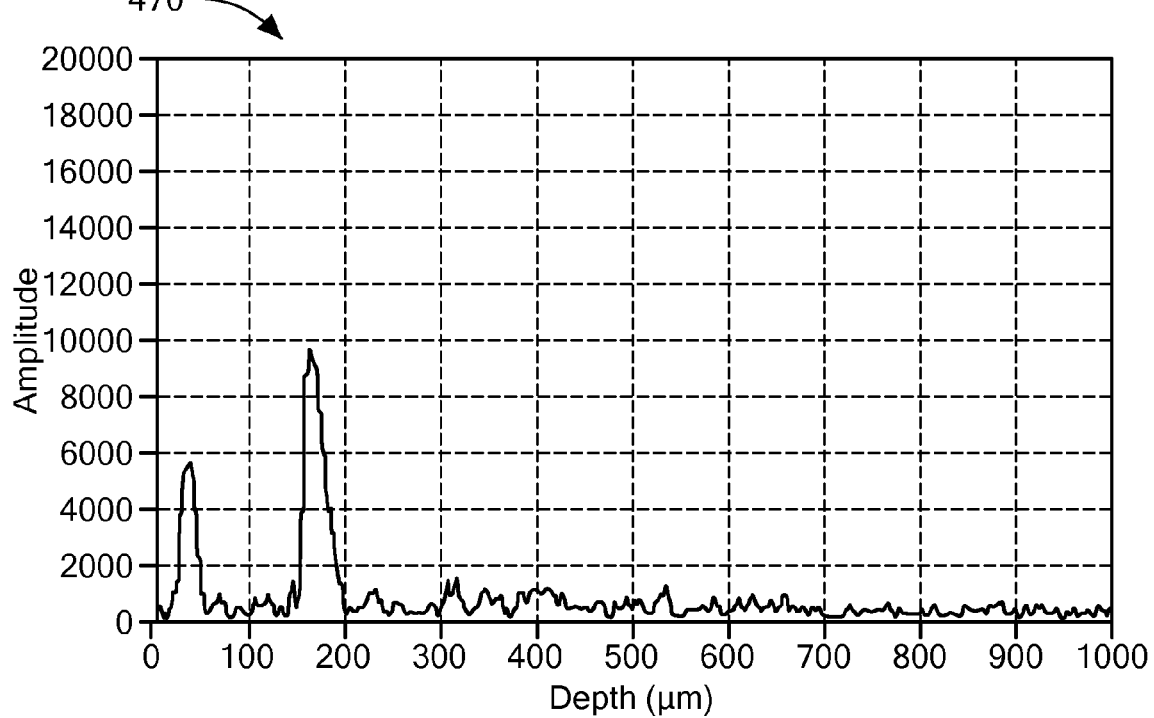
Figure 4C:
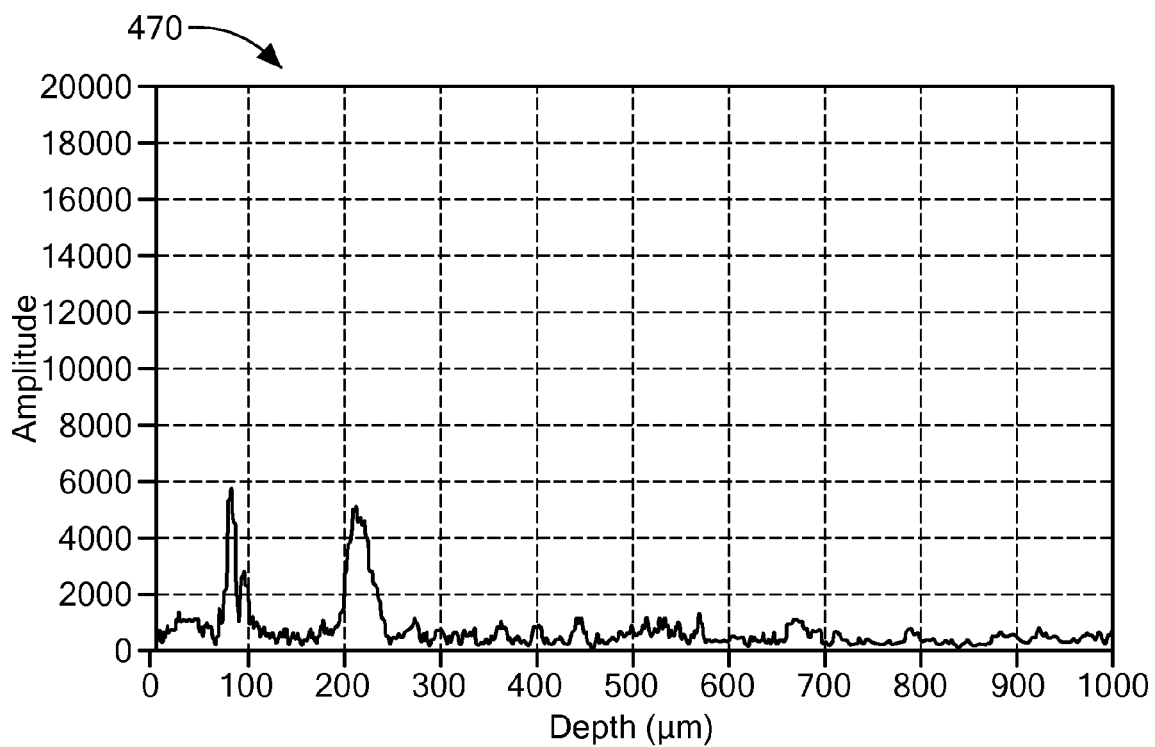
Figure 4D:
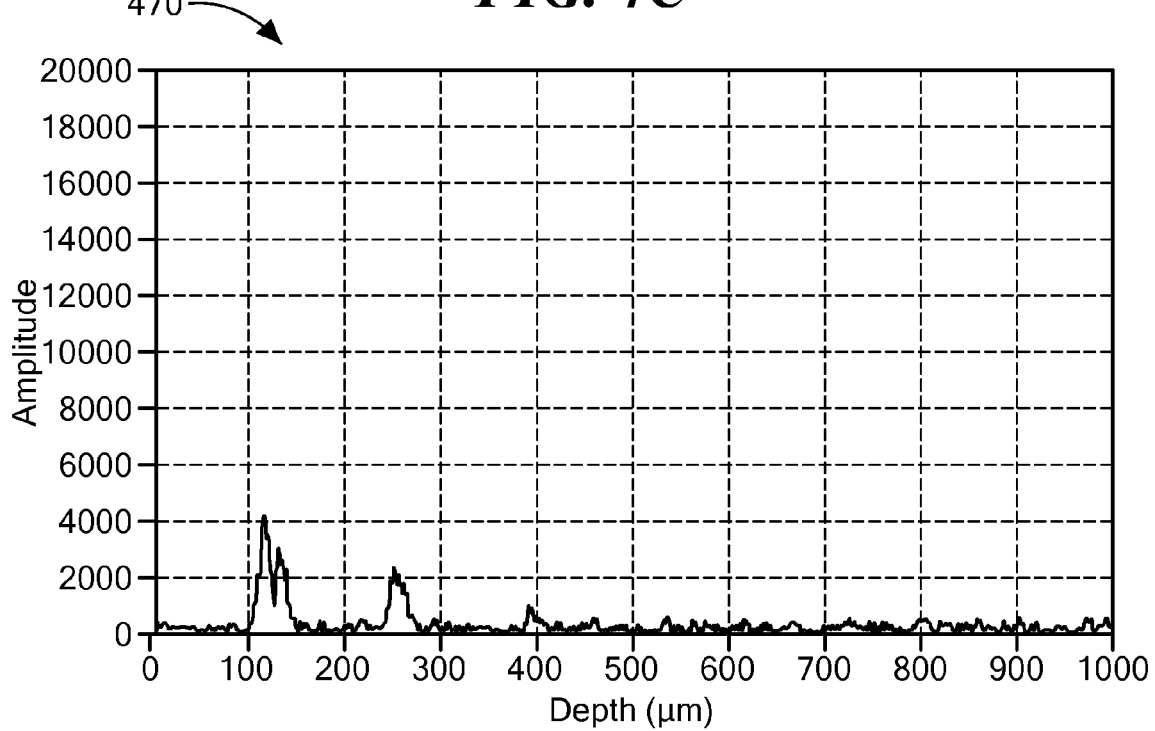

FIG. 3 shows a flowchart depicting salient steps in accordance with diagnostic methods of the present invention. Otoscope tip 404 (shown in FIG. 1B) is inserted into the ear of a patient in step 301. The signal beam derived from low-coherence source 422 (shown in FIG. 1A) is used to illuminate (302) tympanic tissue. Light emitted by low-coherence source 422 is preferably infrared light that penetrates tympanic tissue to a significant depth, including traversing the tympanic membrane completely. In some embodiments of the invention, light emitted by low-coherence source 422 is in the near infrared, and, in some embodiments of the invention, low-coherence source 422 is a superluminescent diode. In an LCI otoscope, each LCI measurement retrieves a depth-resolved "reflectance" at the location of the probing beam and along the direction of the LCI fiber probe (axis-scan). As the term "reflectance" is used herein, the term subsumes scattering, and is not limited to a rigorous meaning of "reflectance" as the term is used in the optical arts.

Using LCI or OCT modality, scattering from the path of low-coherence illumination of the tympanic membrane is measured interferometrically (303) as a function of distance into the ear relative to a fiducial reference point. This profile represents the one-dimensional structural scattering information of the middle-ear. Since the axial depth-scan is fast, relative to small lateral movements between the speculum and the ear, multiple axial-scans can be acquired rapidly, corresponding to a specific set of sampling data that can be analyzed by a computer or reconstructed to produce a cross-section type of "image" associated with the continuous trace of these sampled regions. This information facilitates the detection of tissue structures including the eardrum, ossicles, and the presence of a biofilm.

Pressure in the ear canal is then varied (302), whether by insufflation by means of insufflation bulb, or by means of a mechanical pump. Pressure may be varied in a repeating periodic waveform, which may be sinusoidal, or any other temporal shape. An example of a periodic pressure waveform, in this context, is a sound wave. Pressure in the ear canal may be greater than, or less than, atmospheric pressure, or both, during the course of variation of the pressure. The interferometer signal is recorded (305) with variation in pressure, and the pressure dependence of the signal, at a single transverse position, or at a plurality of positions, is analyzed (306) to derive diagnostic information, as further discussed herein. Any signal analysis methods, such as Fourier decomposition, detection synchronous a cyclical pressure variation, etc., may be employed to improve the ratio of meaningful signal to noise. Independent measures of motion of the otoscope itself, derived, for example, from an accelerometer, may be used to remove signal artifacts, as known to persons of ordinary skill in the art.

FIGS. 4A-4D shows a time sequence of LCI depth scans of a normal eardrum during pressure modulation of the ear canal. As pressure is increased, the displacement (distance from the fiducial reference to the first peak 470) of the eardrum also increases.

An important component of the LCI otoscope is the fiber-optic LCI probe. It is preferably miniaturized to avoid blocking the field of the view of the otoscope (~2.5 mm in diameter), and be flexible enough to adapt to the curved shape of the ear speculum. Because of its dual role as an optical source and receiver, it should produce a collimated beam or a weakly focused beam with a focus approximately the distance between speculum tip and the eardrum (~3-5 mm). A divergent beam will deteriorate the collection efficiency of the back-reflected optical signal. These requirements are achieved by fusion-splicing a gradient index (GRIN) fiber (which acts as a focusing element) on to the end of a single mode fiber (SMF) connected to the sample arm of the LCI interferometer. The GRIN fiber lens face is then polished to attain the appropriate angle and total GRIN fiber length.

Within the scope of the present invention, the LCI otoscope may be replaced by an OCT otoscope which adds a transverse scanning mechanism to the LCI fiber probe. This can be done by a number of lateral translation mechanisms (piezoelectric, electrostatic), or by rotating the optical elements to produce circular scans directed at right-angles from the long axis of the fiber. In this latter mode, the probe behaves effectively like a catheter-endoscope.

Software employed with an LCI/OCT system in accordance with the present invention may include a core software package used to drive the system, collect, and store the LCI depth scans and OCT images. Other modules may provide for improved visualization and rendering the data, and also for automating the classification process of diagnosis. Intelligently designed software can differentiate between normal and diseased ears. In the presented case of detection biofilms in the middle ear, the presence of a biofilm on the inner surface of the tympanic membrane increases the effective optical pathlength, and the optical scattering will reveal a thicker, more irregular membrane, compared to the thin, smooth membrane of a normal ear.

The LCI/OCT data is collected over a wide field, or for several seconds of acquisition time, as a typical middle-ear cavity is one cubic centimeter in size. With such a high-resolution imaging modality and a large data set, there is a need to quickly process and interpret the data in real-time.

The software of the instrument is currently written in commercially-available software (National Instruments LabView, and Mathworks Matlab). The interface of the software including the graphical user interface (GUI) and the interface with the various drivers and is designed in Labview while the data processing core is realized with integrated Labview and Matlab packages. The software package can be divided into three main components. The first part, Data Acquisition, is used to drive/control the instrument, and acquire the video signal of the otoscope and the raw LCI/OCT data from the detector. The second part is the Initial Data Analysis/Display, which is used to process the raw LCI/OCT data into a more traditional OCT-like image by correcting for dispersion and other non-linear optical aberrations.

Classification algorithms specific to the ear pathology employs vivo LCI data from human ears and may be used to automatically determine, in the case of biofilm detection, the thickness and surface features of the tympanic membrane with and without a biofilm present. Data provided to the clinical user may include tympanic membrane thickness and likelihood of a biofilm being present, based on age-matched control measurements. Parameters that may be derived include such geometrical characteristics as tympanic bulging, and the dependence upon ear canal pressure may be used to quantify tympanic membrane mobility.

In accordance with certain embodiments of the present invention, aspects of quantitative pneumatic otoscopy described herein may be implemented as a computer program product for use with a computer system. Such implementations may include a series of computer instructions fixed either on a tangible medium, which is preferably non-transient and substantially immutable, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The embodiments of the invention described above are intended to be merely exemplary; numerous variations and modifications will be apparent to those skilled in the art. All such variations and modifications are intended to be within the scope of the present invention as defined in any appended claims.

We claim:

1. A pneumatic otoscopic imaging system comprising:
 a. a source of light;
 b. a hand-held otoscope for abutment with an ear canal for directing the light to ear tissue and for collecting scattered light from the ear tissue;
 c. an interferometer for combining the scattered light from the ear tissue with a reference beam for generating an interferometry signal;
 d. a pneumatic port coupled to the hand-held otoscope for governing a pressure within the ear canal;
 e. a pump for varying the pressure within the ear canal;
 f. one of a pressure sensor and a pump controller for generating a pressure signal; and
 g. a processor for receiving the interferometry signal and the pressure signal and for generating therefrom a quantitative characterization of the ear tissue under a specified condition of pressure within the ear canal.

2. The pneumatic otoscopic imaging system in accordance with claim 1, further comprising a controller for modulating a pressure at the pneumatic port and thus the pressure within the ear canal.

3. The pneumatic otoscopic imaging system in accordance with claim 1, wherein the pressure within the ear canal exceeds atmospheric pressure.

4. The pneumatic otoscopic imaging system in accordance with claim 1, wherein atmospheric pressure exceeds the pressure within the ear canal.

5. The pneumatic otoscopic imaging system in accordance with claim 1, wherein the controller includes an insufflation bulb.

6. The pneumatic otoscopic imaging system in accordance with claim 1, wherein the controller includes an automated controller.

7. The pneumatic otoscopic imaging system in accordance with claim 1, wherein the controller includes a pneumatic piston.

8. The pneumatic otoscopic imaging system in accordance with claim 1, wherein the controller includes an acoustic transducer.

9. The pneumatic otoscopic imaging system in accordance with claim 1, wherein the source of light is a source of low-coherence light.

10. The pneumatic otoscopic imaging system in accordance with claim 1, wherein the source of light is a characterized by a central wavelength, and wherein the central wavelength is swept as a function of time.

11. The pneumatic otoscopic imaging system in accordance with claim 1, wherein the reference beam is derived from the source of light.

12. The pneumatic otoscopic imaging system in accordance with claim 1, wherein the reference beam is derived from a reflection within a path traversed by the light en route from the source to the ear tissue.

13. The pneumatic otoscopic imaging system in accordance with claim 1, further comprising an optical fiber for coupling light from the source of low-coherence light to the hand-held otoscope.

14. The pneumatic otoscopic imaging system in accordance with claim 1, wherein the source of light is a superluminescent diode.

15. The pneumatic otoscopic imaging system in accordance with claim 1, wherein light includes an infrared component.

16. The pneumatic otoscopic imaging system in accordance with claim 15, wherein the infrared component of the light is a near-infrared component.

17. The pneumatic otoscopic imaging system in accordance with claim 1, wherein the source of light is disposed within a core imaging unit.

18. The pneumatic otoscopic imaging system in accordance with claim 17, wherein the interferometer is also disposed within the core imaging unit.

19. The pneumatic otoscopic imaging system in accordance with claim 1, further comprising a camera for imaging scattering from a surface of at least one of the ear canal and a tympanic membrane.

20. The pneumatic otoscopic imaging system in accordance with claim 1, further comprising a pressure sensor for measuring instantaneous pressure within the ear canal.

21. The pneumatic otoscopic imaging system in accordance with claim 1, further comprising an accelerometer for tracking relative motion between the hand-held otoscope and the ear tissue.

22. A hand-held pneumatic otoscope comprising:
   a. an otoscopic tip for insertion into an ear canal;
   b. focusing optics for directing light to ear tissue via the ear canal and for collecting scattered light from the ear tissue;
   c. a pneumatic port for modulating a pressure within the ear canal;
   d. a pressure sensor for measuring the pressure within the ear canal and for generating a pressure signal; and
   e. an optical coupler for directing the scattered light to an interferometer for interfering the scattered light from the ear tissue with a reference beam to generate an interference signal under a specified condition of pressure within the ear canal; and
   f. a processor for receiving the interference signal and the pressure signal and for generating therefrom a quantitative characterization of the ear tissue under a specified condition of pressure within the ear canal.

23. The hand-held pneumatic otoscope in accordance with claim 22, wherein the light is coupled from a source remote with respect to the hand-held pneumatic otoscope.

24. The hand-held pneumatic otoscope in accordance with claim 23, wherein the light is coupled from the remote source via an optical fiber.

25. The hand-held pneumatic otoscope in accordance with claim 22, further comprising a pressure sensor adapted for measuring air pressure in the ear canal.

26. The hand-held pneumatic otoscope in accordance with claim 22, further comprising a controller for modulating pressure in the ear canal.

27. The hand-held pneumatic otoscope in accordance with claim 22, further comprising an automated controller for modulating pressure in the ear canal.

28. The hand-held pneumatic otoscope in accordance with claim 22, further comprising an insufflation bulb for manually modulating pressure in the ear canal.

29. The hand-held pneumatic otoscope in accordance with claim 22, further comprising a pump for modulating pressure in the ear canal.

30. The hand-held pneumatic otoscope in accordance with claim 22, further comprising a camera for imaging scattering from a surface of at least one of the ear canal and a tympanic membrane.

31. A method for characterizing a tympanic membrane of a person, the method comprising:
   a. illuminating the tympanic membrane of an ear of a person with a broadband optical beam, the ear of the person having an ear canal;
   b. interfering light scattered by the tympanic membrane with a reference beam for generating an interferometric signal;
   c. varying pressure within the ear canal; and
   d. deriving a derivative of a displacement, with respect to pressure within the ear canal, of a position on the tympanic membrane relative to a fiducial position; and
   e. processing the interference signal and the pressure signal and generating therefrom a quantitative characterization of the ear tissue under a specified condition of pressure within the ear canal.

32. The method in accordance with claim 31, further comprising mapping the distensibility in three dimensions across and through the tympanic membrane.

33. The method in accordance with claim 31, further comprising diagnosing movement of ossicles based in tympanic membrane response to sound waves.

34. A method for characterizing at least one of biofilm adjacent to a tympanic membrane of a person and an effusion in a middle ear of the person, the method comprising:
   a. illuminating the tympanic membrane of an ear of a person with a broadband optical beam, the ear of the person having an ear canal;
   b. interfering light scattered by the tympanic membrane with a reference beam for generating an interferometric signal;
   c. varying pressure within the ear canal;
   d. recording the interferometric signal as a function of a pressure signal;
   e. processing the interferometric signal and the pressure signal and generating therefrom a quantitative characterization of any biofilm adjacent to the tympanic membrane and any effusion within the middle ear of the person under a specified condition of pressure within the ear canal; and
   f. ascertaining a specified parameter of the biofilm adjacent to the tympanic membrane and the effusion within the middle ear of the person on the basis of the interferometric signal at more than a single value of the pressure within the ear canal.

35. The method in accordance with claim 34, wherein the specified parameter is a measure of geometrical thickness of the biofilm.

36. The method in accordance with claim 34, wherein the specified parameter is a measure of viscosity.

37. The method in accordance with claim 34, further comprising diagnosing an ear pathology based on the specified parameter.

38. The method in accordance with claim 37, wherein the ear pathology is chronic otitis media.

39. A method for measuring tympanic membrane mobility of a tympanic membrane of a person, the method comprising:
   a. illuminating the tympanic membrane with a broadband optical beam via an ear canal of the person;
   b. interfering light scattered by the tympanic membrane with a reference beam derived from the broadband optical beam to generate an interferometric signal;
   c. modulating an air pressure internal to the ear canal;
   d. processing the interferometric signal and the pressure signal and generating therefrom a quantitative characterization of the tympanic membrane under a specified condition of pressure within the ear canal;
   e. quantifying a geometrical characteristic of the tympanic membrane as a function of air pressure in the ear canal based on the interferometric signal; and f. deriving tympanic membrane mobility based on the quantified geometrical characteristic.

40. The method in accordance with claim 39, wherein the geometrical characteristic is a displacement relative to a fiducial reference surface.

41. The method in accordance with claim 39, wherein the geometrical characteristic is a bulging of the tympanic membrane.

42. The method in accordance with claim 39, further comprising:
 a. ascertaining a specified parameter of any biofilm adjacent to the tympanic membrane on the basis of the interferometric signal; and
 b. diagnosing an ear pathology based on the specified parameter.

43. The method in accordance with claim 42, wherein the ear pathology is otitis media.

44. The method in accordance with claim 39, further comprising:
 a. ascertaining a specified parameter of any middle ear effusion on the basis of the interferometric signal; and
 b. diagnosing an ear pathology based on the specified parameter.

\* \* \* \* \*